United States Patent
Wei-Yu et al.

(12)

(10) Patent No.: US 6,689,867 B1
(45) Date of Patent: Feb. 10, 2004

(54) PLACENTA DERIVED APOPTOTIC FACTOR

(75) Inventors: Lo Wei-Yu, Taipei (TW); Hsieh Shie-Liang, Taipei Shien (TW)

(73) Assignee: Anawrahta Biotech Co., Ltd., Taipei-Shien (TW)

( * ) Notice: Subject to any disclaimer, the term of this patent is extended or adjusted under 35 U.S.C. 154(b) by 0 days.

(21) Appl. No.: 09/684,327

(22) Filed: Oct. 10, 2000

(51) Int. Cl.⁷ ............................................. C07K 17/00
(52) U.S. Cl. ..................................................... 530/350
(58) Field of Search ........................ 424/184.1, 185.1, 424/192.1, 193.1, 277.1; 514/2; 530/350

(56) References Cited

FOREIGN PATENT DOCUMENTS

WO    WO 99/57270    * 11/1999

OTHER PUBLICATIONS

Dermer, Bio/Technology, Vol 12, p. 320, Mar. 1994.*
Bowie et al., Science, 1990, 247:1306–1310.*
Burgess et al., J of Cell Bio. 111:2129–2138, 1990.*
Lazar et al., Molecular and Cellular Biology, 1988, 8:1247–1252.*
Bork, Genome Research, vol. 10, pp. 398–400, 2000.*
Accession #AAY32197, Feb. 15, 2000.*
Accession #O00559. Aug. 20, 2001.*
Nakashima et al., "Inhibition of cell growth and induction of apoptotic cell death by the human tumor–associated antigen RCAS", *Nature Medicine*, vol. 5, No. 8, pp. 938–942 (Aug. 1999).
Sonoda et al., "A Novel Tumor–Associated Antigen Expressed in Human Uterine and Ovarian Carcinomas", *Cancer*, vol. 77, No. 8, pp. 1501–1509 (Apr. 15, 1996).
Sonoda et al., "Tumor–associated Antigen 22–1–1 Expression in the Uterine Cervical Squamous Neoplasias", *Clinical Cancer Research*, vol. 4, pp. 1517–1520 (Jun. 1998).

* cited by examiner

*Primary Examiner*—Susan Ungar
(74) *Attorney, Agent, or Firm*—Fish & Richardson P.C.

(57) ABSTRACT

The invention provides the nucleic acid and amino acid sequences of a novel human tumor-associated antigen, planenta derived apoptotic factor (PDAF), and the use of these sequences in the treatment of disorders associated with immune and cell proliferation.

11 Claims, 13 Drawing Sheets

```
       9            18           27            36           45           54
5' ATG GCC ATC ACC CAG TTT CGG TTA TTT AAA TTT TGT ACC TGC CTA GCA ACA GTA ---
    M   A   I   T   Q   F   R   L   F   K   F   C   T   C   L   A   T   V

TM
      63           72           81           90           99          108
--- TTC TCA TTC CTA AAG AGA TTA ATA TGC AGA TCT GGC AGA GGA CGG AAA TTA AGT ---
    F   S   F   L   K   R   L   I   C   R   S   G   R   G   R   K   L   S

TM 117          126          135          144          153          162
--- GGA GAC CAA ATA ACT TTG CCA ACT ACA GTT GAT TAT TCA TCA GTT CCT AAG CAG ---
    G   D   Q   I   T   L   P   T   T   V   D   Y   S   S   V   P   K   Q 171          180          189          198          207          216
--- ACA GAT GTT GAA GAG TGG ACT TCC TGG GAT GAA GAT GCA CCC ACC AGT GTA AAG ---
    T   D   V   E   E   W   T   S   W   D   E   D   A   P   T   S   V   K
```

FIG. 1A

```
     225            234            243            252            261            270
ATC GAA GGA GGG AAT GTG GCA ACA CAA AAT TCT TTG GAA CAA CTG
 |   |   |   |   |   |   |   |   |   |   |   |   |   |   |
 I   E   G   G   N   V   A   T   Q   Q   N   S   L   E   Q   L 279            288            297            306            315            324
GAA CCT GAC TAT TTT AAG GAC ATG ACA CCA ACT ATT AGG AAA ATT
 |   |   |   |   |   |   |   |   |   |   |   |   |   |   |
 E   P   D   Y   F   K   D   M   T   P   T   I   R   K   I 333            342            351            360            369            378
GTT ATT AAG AAG AGA GAA CCA TTG AAT TTT GGC ATC CCA GAT GGG AGC ACA GGT
 |   |   |   |   |   |   |   |   |   |   |   |   |   |   |   |   |   |
 V   I   K   K   R   E   P   L   N   F   G   I   P   D   G   S   T   G 387            396            405            414            423            432
TTC TCT AGT AGA TTA GCA GCT ACA CAA GAT CTG CCT TTT ATT CAT CAG TCT TCT
 |   |   |   |   |   |   |   |   |   |   |   |   |   |   |   |   |   |
 F   S   S   R   L   A   A   T   Q   D   L   P   F   I   H   Q   S   S
```

FIG. 1B

```
     441            450            459            468            477            486
GAA  TTA  GGT  GAC  TTA  GAT  ACC  TGG  CAG  GAA  AAT  ACC  AAT  GCA  TGG  GAA  GAA  GAA
 E    L    G    D    L    D    T    W    Q    E    N    T    N    A    W    E    E    E 495            504            513            522            531            540
GAA  GAT  GCA  GCC  TGG  CAA  GCA  GAA  GAA  GTT  CTG  AGA  TCC  AGG  ACC  AAT  GTA  TGT
 E    D    A    A    W    Q    A    E    E    V    L    R    S    R    T    N    V    C 549            558            567            576            585            594
TTA  CTC  TGC  TCT  CTC  TTT  CAT  CAT  CCC  ACT  CCT  ACC  TCC  ACT  CCC  TAC  ATT
 L    L    C    S    L    F    H    H    P    T    P    T    S    T    P    Y    I 603            612            621            630            639            648
AAC  CAA  TCA  GTA  AAG  ATA  GAG  AGA  GTG  AGT  CTG  GGT  CAG  TGG  AGT  TAC  GGA  AAG
 N    Q    S    V    K    I    E    R    V    S    L    G    Q    W    S    Y    G    K
```

FIG. 1C

```
        657              666              675              684              693              702
AGT AAG GAA CAG CAG AAA CTA GCA GAC AGA GAA AAG AGA GCA GAA CAA CAA
         |   |   |   |   |   |   |   |   |   |   |   |   |   |   |   |
         S   K   E   Q   Q   K   L   A   D   R   E   K   R   A   A   E   Q   Q 711              720              729              738              747              756
AGG AAG AAA ATG GAA AAG GAA GCA CAA CGG CTA ATG AAG AAG GAA CAA AAC AAA
 |   |   |   |   |   |   |   |   |   |   |   |   |   |   |   |   |   |
 R   K   K   M   E   K   E   A   Q   R   L   M   K   K   E   Q   N   K
                                     DIM 765              774
ATT GGT GTG AAA CTT TCA TAA 3'
 |   |   |   |   |   |   |
 I   G   V   K   L   S   *
```

Box region: a novel peptide consists of 45 amino acids in the PDAF protein
Shadow region: ATP-GTP binding site motif
Underline region: TM - transmembrane domain
DIM - coiled coil structure and dimeric domain

FIG. 1D lane1 & 5: uncut
lane2 & 6: EcoRI cut
lane3 & 7: Bgl II cut
lane4 & 8: Apo I cut
M1: GeneRuler™ 1Kb DNA Ladder
M2: GeneRuler™ 100bp DNA Ladder Plus PDAF    185  LLFHPTPTSTPYINQSVKIERVSLGQWS    213
             L+  HH  P    ++ S+ I+R+  GQW+
PIG-B  256  LILHFLPVGFVTLSLSLMIDRIFFGQWT   284

Identities = 10/29 (34%)
Positives = 17/29 (58%)

FIG. 3

M: 100 bp DNA marker
lane1: MCF7
lane2: HT29
lane3: RD
lane4: A375
lane5: placenta

PLACENTA DERIVED APOPTOTIC FACTOR

BACKGROUND OF THE INVENTION

1. Field of the Invention

The present invention relates to a novel human tumor-associated antigen, designated as placenta derived apoptotic factor (PDAF), and the genes thereof.

2. Description of the Prior Art

A number of cancer-specific genetic markers and tumor-associated antigens have been identified. It is found that tumor-associated antigens are mostly surface molecules that are expressed in tumor cells, instead of the cells of non-tumor tissues. Tumor-associated antigens have been characterized either as membrane proteins or altered carbohydrate molecules of glycoproteins and glycolipids. They make tumor cells immunologically distinct from normal cells, which are useful as diagnostic and therapeutic targets for human cancers.

Some tumor-associated antigens have been disclosed in prior references. For instance, a receptor-binding cancer antigen expressed on SiSo cells (RCAS1) functioning as a tumor-associated antigen, has been described by Takeshi Watanabe et al., 1999, Nature Medicine, Vol. 5, No. 8, pp.938–942. RCAS1 gene does not express in normal cells, but expresses in uterine cervical adenocarcinoma, uterine endomertrial adenocarcinoma, ovarian carcinoma and uterine cervical squamous cell carcinoma (see, Takeshi Watanabe et al., 1996, American Cancer Society, pp.1501–1509; and Hitoo Nakano, 1998, Clinical Cancer Research, vol. 4, pp. 1517–1520). In addition, the RCAS1 gene can also be expressed in esophageal squamous cell carcinoma, gastric adenocarcinoma, colon adenocarcinoma and pancreatic adenocarcinoma. RCAS1 is a protein comprising 213 amino acids. Such protein has an N-terminal transmembrane segments (8–27 amino acids) and a coiled-coil structure in the C-terminal portion (179–206 amino acids), indicating that RCAS1 may be a type II membrane protein or a secreted protein having a structure of dimeric protein. RCAS1 acts as a ligand for a putative receptor present on various human cell lines such as K562 (human chronic myelogeneous leukemia), CCRF-CEM (human T lymphoblast) and Ramos (Burkitt lymphoma) and normal peripheral lymphcytes such as T, B and NK cells. RCAS1 inhibits the growth of receptor-expressing cells and induces apoptotic cell death. Tumor cells may evade immune surveillance by expressing RCAS1 and induce apoptosis in RCAS1 receptor-positive immune cells. RCAS1 plays roles in both tumor-associated antigen and induction of apoptosis of the immune cells.

It is expected that new tumor-associated antigens, similar to the tumor-associated RCAS1 antigen and the nucleic acids coding for the antigens, are useful in diagnosing, preventing, and treating immune disorders, cell proliferation and tumors, particularly cancers.

SUMMARY OF THE INVENTION

One object of the invention is to provide a novel human tumor-associated antigen, designated as placenta derived apoptotic factor (PDAF), which comprises an amino acid sequence of SEQ ID NO:1 and the biologically functional equivalent.

One object of the invention is to provide a polypeptide comprising an amino acid sequence of SEQ ID NO:2 and the variants thereof.

One object of the invention is to provide a fragment of the PDAF, comprising an amino acid sequence of SEQ ID NO:3 and the biologically functional equivalent thereof.

Another object of the invention is to provide the nucleic acid of SEQ ID NO: 4 encoding the polypeptide of SEQ ID NO: 1 and the degenerate sequences thereof. Also, the invention provides the nucleic acid of SEQ ID NO: 5 encoding the polypeptide of SEQ ID NO: 2 and the degenerate sequences thereof; and the nucleic acid of SEQ ID NO: 6 encoding the polypeptide of SEQ ID NO: 3 and the degenerate sequences thereof.

Another object of the invention is to provide an expression vector containing the nucleic acid of SEQ ID NO: 4, and an expression vector containing the nucleic acid of SEQ ID NO: 6. In addition, the invention provides a host cell containing the nucleic acid of SEQ ID NO: 4 and a host cell containing the nucleic acid of SEQ ID NO: 6.

Another object of the invention is to provide a pharmaceutical composition comprising the PDAF of the invention, or the fragments thereof.

Another further object of the invention is to provide transgenic animals, which is introduced with a gene fragment containing the nucleic acid sequence of SEQ ID NO: 4, or a gene fragment containing the nucleic acid sequence of SEQ ID NO: 5, or a gene fragment containing the nucleic acid sequence of SEQ ID NO: 6.

BRIEF DESCRIPTION OF THE DRAWINGS

FIGS. 1A–1D show the amino acid sequence of PDAF (SEQ ID NO:1) and the coding nucleic acid sequence thereof (SEQ ID NO:4).

FIG. 3 shows the similarity between the amino acids 185–213 of PDAF (SEQ ID NO:1) and the amino acids 256–284 of PIG-B (SEQ ID NO:9).

DETAILED DESCRIPTION OF THE INVENTION

Figure 2A:
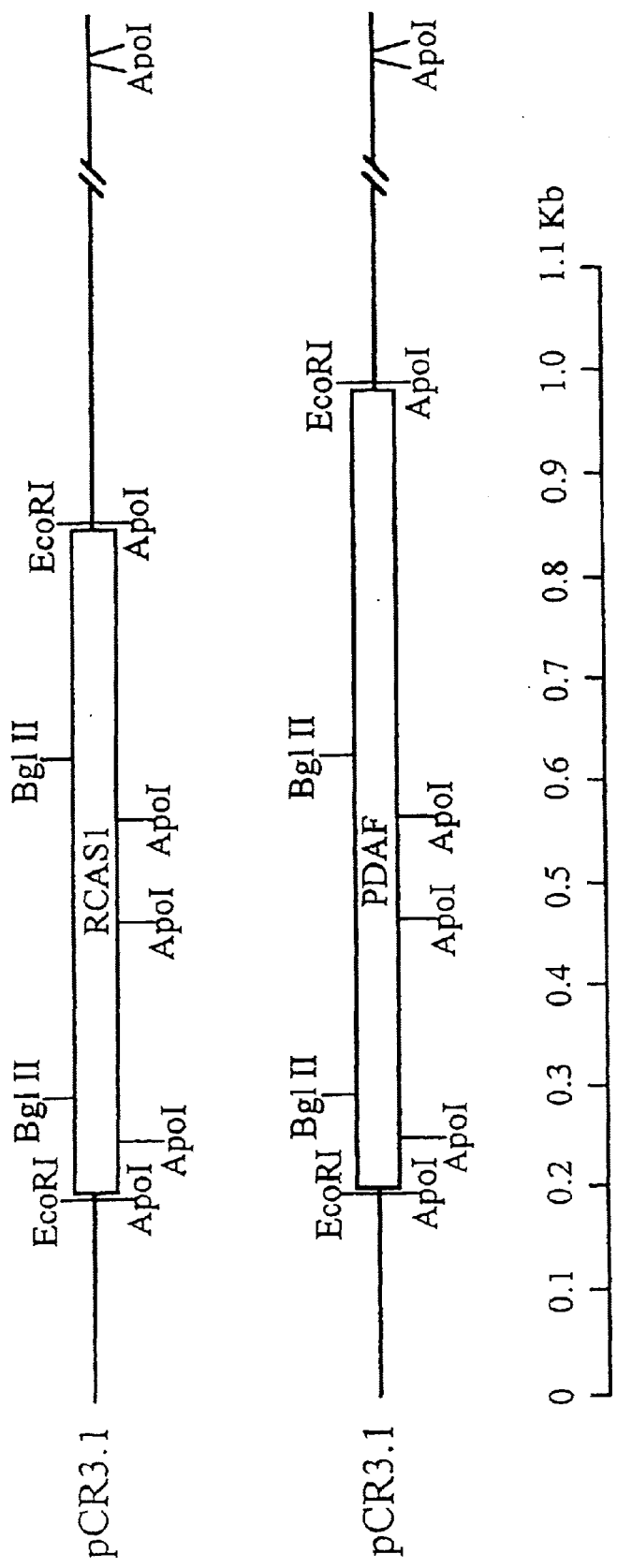
FIGS. 2A–2B show a restriction map of RCAS1 and PDAF.

The present invention features a novel tumor-associated antigen hereinafter designated PDAF and characterized by having a similarity to RCAS1. It is surprisingly found that as compared with RCAS1, the PDAF of the invention shows a higher apoptotic rate to the tumor cells and immune cells.

Definitions

The term "nucleic acid sequence", as used herein, refers to peptide nucleic acid (PNA; The FASEB Journal, 2000, 14:

(1041–1060)) and polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "amino acid sequence", as used herein, refers to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. Amino acid sequence includes an oligopeptide, peptide, polypeptide, or protein sequence, and fragments or portions thereof, and to naturally occurring or synthetic molecules.

The term "variant", as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both.

The term "deletion", as used herein, refers to a change in either amino acid or nucleotide sequence in which one or more amino acid or nucleotide residues, respectively, are absent.

The term "insertion" or "addition", as used herein, refers to a change in an amino acid or nucleotide sequence resulting in the addition of one or more amino acid or nucleotide residues, respectively, as compared to the naturally occurring molecule.

The term "derivative", as used herein, refers to the chemical modification of a nucleic acid. Illustration of such modifications would be replacement of hydrogen by an alkyl, acyl, or amino group. A nucleic acid derivative would encode a polypeptide which retains essential biological characteristics of the natural molecule.

The term "biologically function equivalent", as used herein, refers to a protein having structural, regulatory, or biochemical functions of a naturally occurring molecule.

The term "fusion protein", as used herein, refers to a fusion of a first amino acid sequence encoding a target polypeptide with a second amino acid sequence defining a domain (e.g. polypeptide portion) foreign to and not substantially homologous with any domain of a target protein.

The term "vector", as used herein, refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome.

The term "host cell", as used herein, refers to a cell of a host which can be infected with a vector, such as a palsmid. The hosts suitable for the invention include those commonly and conventionally used in the art.

The term "transgenic animal", as used herein, refers to any animal in which one or more, and preferably essentially all, of the cells of the animal introduced with a foreign gene. The gene is introduced into the animal cell, directly or indirectly by introduction into a precursor of the cell, by way of deliberate genetic manipulation, such as by microinjection or by infection with a recombinant vector. The term genetic manipulation includes not only classical cross-breeding, or in vitro fertilization, but also the introduction of a recombinant DNA molecule, which may be integrated within a chromosome or may be extrachromosomally replicating DNA.

Polypeptides

One object of the invention is to provide a polypeptide, designated as placenta derived apoptotic factor (PDAF), comprising the amino acid sequence as shown in SEQ ID NO:1, see FIGS. 1A–1D, and the biologically functional equivalent thereof.

The PDAF refers to the amino acid sequences of substantially purified PDAF obtained from any species, preferably human, from any source whether natural, synthetic, semi-synthetic, or recombinant.

According to the invention, PDAF comprises 258 amino acids, wherein 213 amino acids of PDAF are completely same as those of RCAS1. The sequence consisting of the 213 amino acids contains a transmembrane domain and a coiled-coil structure and dimeric domain. PDAF of the invention can induce apoptosis to the tumor cells and immune cells.

Another object of the invention is to provide a polypeptide consisting of 45 amino acids (SEQ ID NO:2) and the variants thereof. The 45 amino acids are at the positions 175–219 of PDAF (see FIGS. 1A–1D). As compared with the sequences of RCAS, the 45 amino acids (SEQ ID NO:2) are inserted between amino acids 174 and 175 of RCAS1. Such sequence of 45 amino acids forms a hydrophobic region before the coiled-coil functional structure and dimeric domain of RCAS1. Therefore, the hydrophobic region may affect the structure of the whole protein and thus the PDAF has an improved efficacy than RCAS1. In addition, it is found the amino acids at positions 210–217 in SEQ ID NO:2 are similar to the sequences of ATP-GTP binding site motif of Ras protein. The proto-oncogene ras is an essential gene for the growth and differentiation for various type of cells. Ras is a GTP binding protein which controls the signal transduction by GTP hydrolysis. A signal point mutation in the GTP binding motif of the ras gene accounts for more than 90% of all ras mutations and is present in more than 20% of all solid tumor. Therefore, mutant ras provides a potential target for cancer therapy (see, Journal of Immunotherapy, 1999, 22(2):155–165 and the Journal of Urology, 1999, 162:1519–1526). Given the above, we can reasonably expect that SEQ ID NO:2 encompassing the GTP-ATP binding motif is also important in the growth and differentiation of cells and can be used in the treatment and diagnosis of diseases.

According to the invention, a preferred variant of SEQ IN NO:2 is one having at least 80%, preferably 90%, amino acid sequence similarity to the SEQ ID NO:2. A most preferred variant of SEQ ID NO:2 is one having at least 95% amino acid sequence similarity to SEQ ID NO:2.

One object of the invention is to provide a polypeptide sequence of consisting of the amino acids at positions 175–258 of PDAF (SEQ ID NO:3) and the variant thereof. SEQ ID NO:3 is a functional fragment mainly inducing the apoptosis for immune cells and tumor cells. A preferred variant is one having at least 80%, and more preferably 90%, amino acid sequence similarity to the SEQ ID NO:3. A most preferred PDAF variant is one having at least 95% amino acid sequence similarity to SEQ ID NO:3.

The PDAF of the invention includes the altered sequences and functional equivalents of PDAF, which may be modified by a deletion, insertion, or substitution of amino acid residues.

Nucleic Acids

Another object of the invention is to provide an isolated nucleic acid sequence (SEQ ID NO:4) and the altered sequences thereof, which encode PDAF (SEQ ID NO:1) as shown in FIGS. 1A–1D. PDAF gene is similar to the RCAS1 gene, which consists of 774 DNAs in length. PDAF gene is cloned from human placenta cell line and rhabdomyoma tumor RD cell line.

The invention also provides an isolated nucleic acid sequence (SEQ ID NO: 5) consisting of 135 DNAs and the altered sequences thereof, which encodes the 45 amino acids as shown in SEQ ID NO: 2. The 135 DNAs sequences are inserted between positions 522 and 523 of the RCAS1 sequences. The numbers of such SEQ ID NO: 5 are a multiple of 3 and no translation stop codon exists in the region. Therefore, such a region does not affect the translation of the subsequent amino acid sequences and the length thereof.

The invention also provides an isolated nucleic acid sequence (SEQ ID No: 6) consisting of the nucleic acids at positions 523–774 of the PDAF DNAs and the altered sequences thereof, which encode the polypeptide of SEQ ID NO:3. Such sequence may be the functional fragments of PDAF.

According to the invention, the production of DNA sequences, or fragments thereof, which encode the sequences SEQ ID Nos: 1, 2 and 3 and their derivatives, may use chemical methods well known in the art Alternatively, they may be produced through chemical methods. For example, peptide synthesis can be performed using various solid-phase techniques and automated synthesis may be achieved through a peptide synthesizer, for example, ABI 431A Peptide Synthesizer.

Methods for DNA sequencing which are well known and generally available in the art may be used to practice any embodiments of the invention. The methods may employ such enzymes as the Klenow fragment of DNA polymerase I, Taq polymerase, T7 polymerase, or combinations of recombinant polymerases and proofreading exonucleases such as the ELONGASE or commercially available kits. Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences of the present invention can be engineered using methods generally known in the art in order to alter PDAF encoding sequences for a variety, including but not limited to, alterations which modify the cloning, processing, and/or expression of the gene product.

Expression Vector and Host System

Another object of the invention is to provide an expression vector, containing the nucleic acid sequences as shown in SEQ ID Nos. 4 or 6. In order to express a biologically active PDAF, the nucleic acid sequences encoding PDAF or functional equivalents, may be inserted into appropriate expression vector, i.e., a vector which contains the necessary elements for the transcription and translation of the inserted coding sequence. According to the invention, methods being well known to those skilled in the art may be used to construct expression vectors containing sequences encoding PDAF and appropriate transcriptional and translational control elements. These methods include in vitro recombinant DNA techniques, synthetic techniques, and in vivo genetic recombination.

Another object of the invention is to provide a host cell containing the expression vector containing the nucleic acid sequence as shown in SEQ ID Nos. 4 or 6. According to the invention, a number of host systems may be utilized to contain and express sequences encoding PDAF. These include, but are not limited to, microorganisms such as bacteria transformed with recombinant bacteriophage, plasmid, or cosmid DNA expression vectors; yeast transformed with yeast expression vectors; insect cell systems infected with virus expression vectors; plant cell systems transformed with virus expression vectors or with bacterial expression vectors; or animal cell systems.

Utility

According to the invention, it is surprisingly found that PDAF possesses the features as follows:

(1) As compared with RCAS1, the PDAF induces a higher apoptotic rate to the peripheral blood lymphocyte, native B cell, activated T cell and leukemia cell lines such as Jurkat and TF-1. Therefore, PDAF can be used as a cytotoxic agent for the treatment of leukemia, and/or an immunosuppressive agent for the disorders associated with the need of inhibiting response such as graft versus host diseases, autoimmune diseases and course of transplantation.

(2) In addition, the expression of PDAF is higher than that of RCAS1 in placenta tissue. Moreover, PDAF can induce the apoptosis of the immune cells. Based on the teachings of David A. Clark, 1991, Critical Reviews in Immunology, 11(3,4): 215–247, we can reasonably respect that PDAF can be used in reducing sterility caused by the rejection to sperm and abortion caused by the rejection to fetus tissue.

(3) PDAF can be expressed in the tumor cells. Therefore, we can expect that the antibodies against PDAF can be used in killing the tumor cells expressing RCAS1 or PDAF.

(4) The expression of PDAF is lower than that of RCAS1 in some tumor cells. Therefore, the expression of the PDAF has higher tissue specificity than that of RCAS1. We can thus expect that PDAF can be used in the diagnosis of cancer.

(5) It is known in the art that unimunosuppressive agent can be used in the treatment of hepatitis (see, Crit Rev Immunol, 1991, 11 (3–4):215–247). Therefore, we can reasonably expect that the PDAF of the invention may be used in treating hepatitis.

Given the above, the PDAF of the invention can be used in the treatment and diagnosis of the diseases associated with cell proliferation and immune response.

Pharmacezitical Composition

The invention also provides a pharmaceutical composition comprising the polypeptides as shown in SEQ ID NO:1 or 3, particularly for use in treating cell proliferation or inhibiting immune response. The pharmaceutical composition may contain suitable pharmaceutically-acceptable carriers, and optionally excipients and auxiliaries.

The pharmaceutical compositions of the invention may be manufactured in a manner that is known in the art, e.g., by means of conventional methods comprising the steps of mixing, dissolving, granulating, dragee-making, levigating, emulsifying, encapsulating, entrapping, and/or lyophilizing steps.

The pharmaceutical compositions of the invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

Transgenic Animals

The invention also provides transgenic animals, which is introduced with a gene fragment containing the nucleic acid sequence of SEQ ID NO: 4, or a gene fragment containing the nucleic acid sequence of SEQ ID NO: 5, or a gene fragment containing the nucleic acid sequence of SEQ ID NO: 6. According to the invention, the transgenic animals may be any convenient animals, such as non-human mammal, for example as used in laboratory test procedures such as rodents, e.g., mice or rats; and for example as used for producing organs or tissues for transplantation, such as pigs and horses. The transgenic animals of the invention are conveniently obtained by introducing into animals the genes of the invention using conventional and convenient genetic manipulation techniques such as by microinjection or by infection with a recombinant vector. The gene may be directly or indirectly intoruced into a cell or all the cells of an animal by introduction into a precursor cell. The genetic manipulation techniques include classical cross-breeding, in vitro fertilization, introduction of a recombinant DNA molecule, which may be integrated within a chromosome or may be extrachromosomally replicating DNA. The genes of the invention include the gene fragments containing the nucleic acid sequences of SEQ ID NOS: 4, 5, AND 6, respectively.

According to the invention, the transgenic animals have non-specific immunosuppressive activity due to an introduction of the genes of the invention. Therefore, the transgenic animals may be used as organ or tissue sources for transplantation, which is more acceptable to humans.

The following Examples are offered by way of illustration and not by way of limitation.

EXAMPLES

Example 1

Production of PDAF Cloning of Human PDAF Gene

The placental tissues were grinded and mixed using a Glass grinder (Wheaton) in RNAZOL™ B solution (RNA isolation reagent). 0.1 ml of chloroform was added to the resulting solution and then the solution was placed on ice for 5 minutes. The resulting solution was centrifuged at 12,000×g at 4° C. for 15 minutes. Take 0.5 ml of the upper water layer and then add 0.5 ml of isopropanol to the layer. After completely mixing, the resulting solution was placed on the ice for 15 minutes and then centrifuged at 12,000×g at 4° C. for 15 minutes to precipitate RNA. 1 ml of 75% alcohol was added to the precipitates to remove the salt in the RNA precipitates. The RNA precipitates were naturally dried in the air and then solved in appropriate amount of sterilized water. The $OD_{260}$ was determined for quantifying the RNA.

The reverse transcription reaction was performed using total RNA of placenta and oligo-d(T)$_{12-18}$ primers. The resulting first strand cDNA was bound to the complementary RNA to form a nucleic acid molecule. The nucleic acid molecule was treated with RNase H to obtain a primer for use in the synthesis of the second strand cDNA. Said cDNA was synthesized by using the primer and polymerase. The resulting cDNA was ligated into plasmid pCR3. 1. The plasmid pCR3. 1 was subsequently transformed into the host cells *F. Coli* DHScz. The host cells were transferred to the nitrocellulose membrane and lysed by using buffer containing strong basic and SDS to release the plasmid DNA. The plasmid DNA was treated with UV for fixing such DNA in the nitrocellulose membrane. The degenerated sequence of the peptide sequence GXXXXGKS (SEQ ID NO: 7) of ATP-GTP binding site was used as the DNA probe to select the desired plasmid DNA of the host cells through hybridization reaction. The selected host cells were cultured and then the plasmid of the host cells was extracted. The DNA was sequenced through restriction map assay using various restriction enzymes or through automatic sequencing of double strand DNA using primer T7 and pCR3. 1 reverse primer.

Figure 2B:
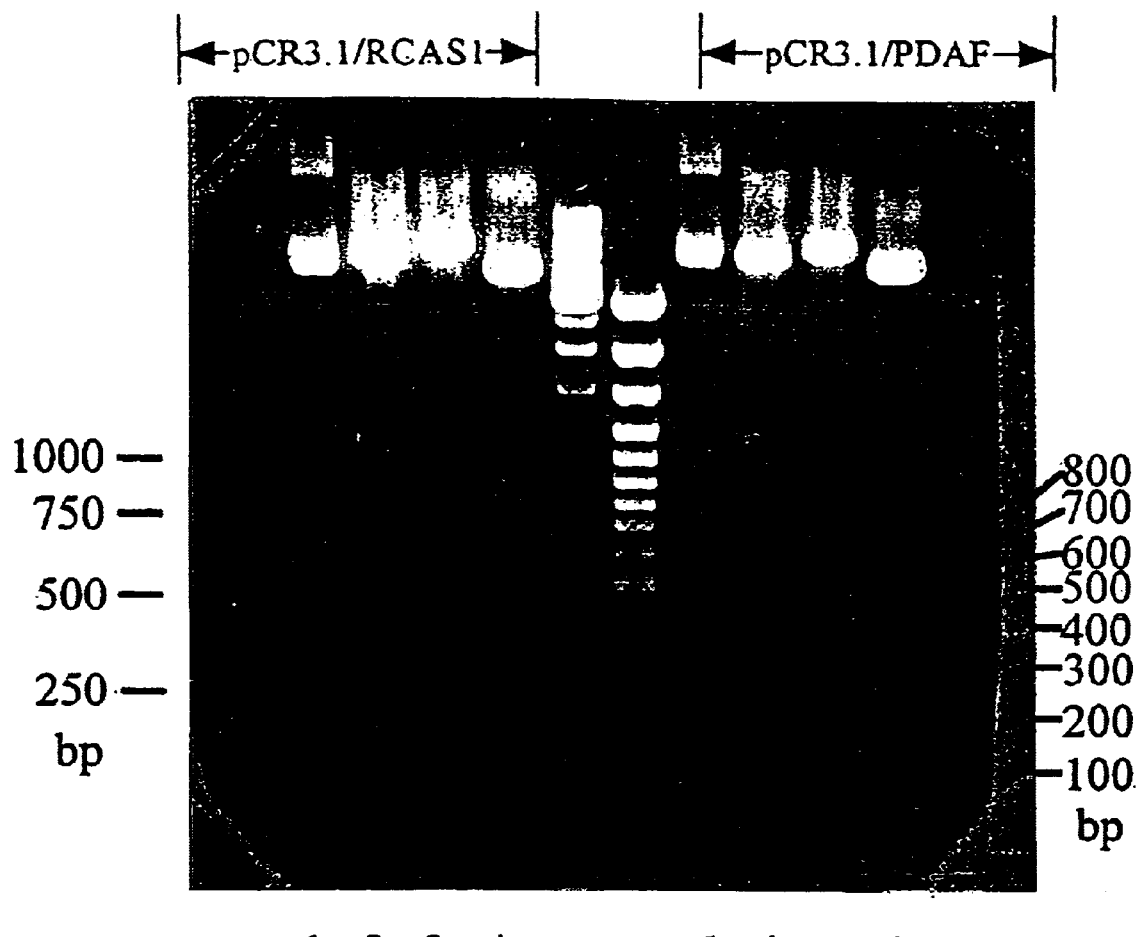

The sequenced DNA was analyzed by using DNASIS-Macv 2.0 software. After comparing with the sequences in Genebank, we have not found that any gene sequences are same as the sequence of the PDAF of the invention. However, it is found that the protein traslation region of the novel PDAF gene is similar to that of RCAS1. As shown in FIGS. 1A–1D, the protein translation region of the PDAF gene has 774 nucleic acids in length (SEQ ID NO:4. Further, the restriction maps (see FIGS. 2A–2B) of PDAF and RCAS1 prove that the PDAF gene is indeed different from RCAS1.

The protein translation region of the novel PDAF gene has additional 135 nucleic acids (SEQ ID NO: 5). The remaining 642 nucleic acids of the PDAF are completely same as that of RCAS1. In addition, it could not be found the sequences as the same as the above-mentioned 135 nucleic acids in the Genebank. Said sequence consisting of 135 nucleic acids is inserted between positions 522 and 523 of the sequence of RCAS 1.

Figure 4:
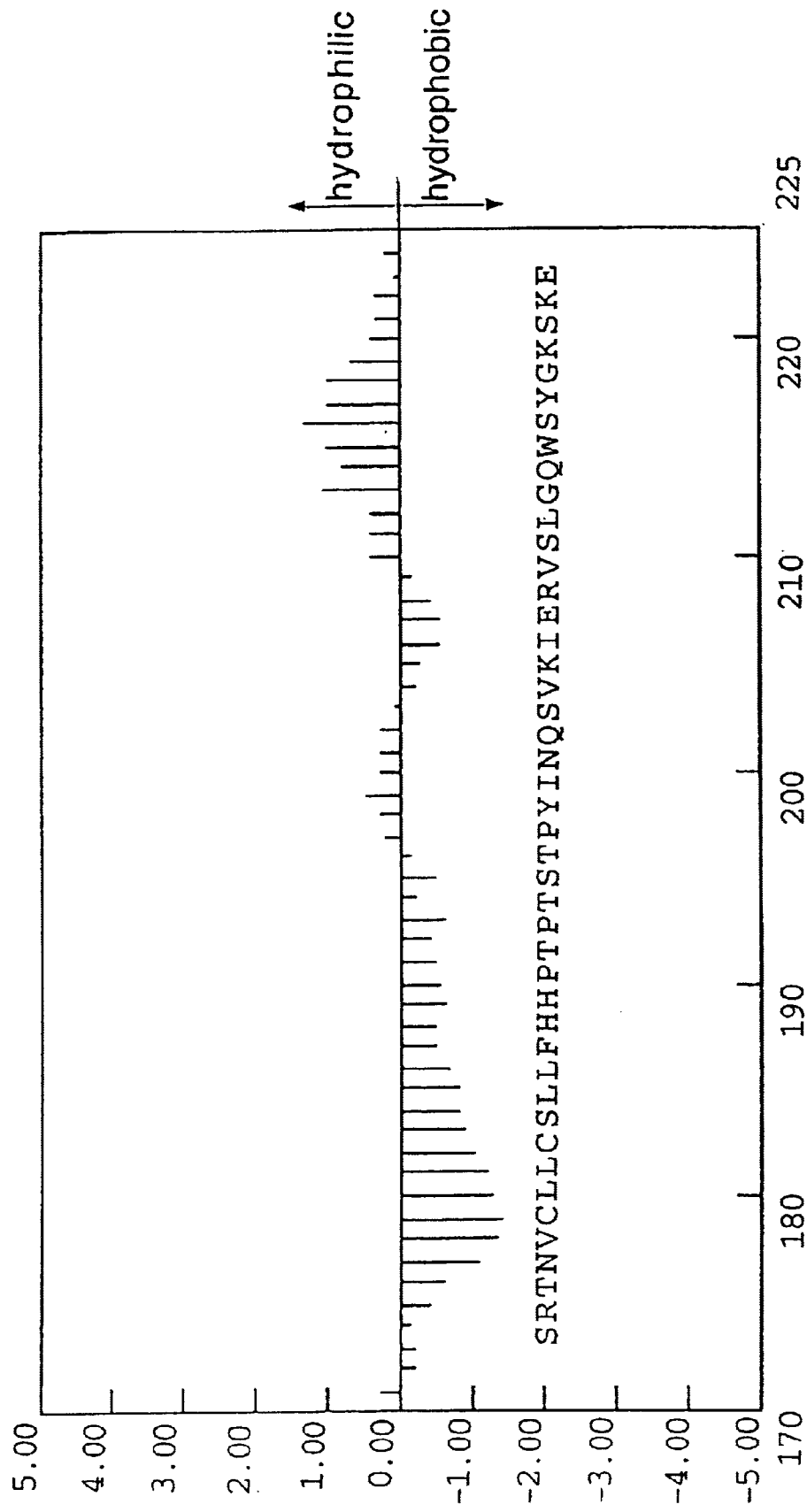
FIG. 4 shows hydropathy analysis of PDAF.

The sequence of 135 nucleic acids encodes a sequence consisting of 45 amino acids (SEQ ID NO. 2). After checking the Genebank, no similar sequences can be found. Only the sequence of amino acids 256–284 of the phosphatidylinositol glycon of complementation class B (PIG-B) in the endoplasmic reticulum (ER) has low similarity to the sequence of 45 amino acids (see FIG. 3). Therefore, said sequence of 45 amino acids is a new sequence. Through the analysis of DNAISIS-Mac v.2.0 software, it is found that the sequence of 45 amino acids is a highly hydrophobic peptide (see FIG. 4). The amino acids 210–217 (GQWSYGKS) of said peptide are highly similar to the sequence ((AIG) XXXXGK(S/T))(SEQ ID NO:8) of ATP-GTP binding site motif of Ras protein.

Expression of PDAF in Tumor Cell Lines

Figure 5:
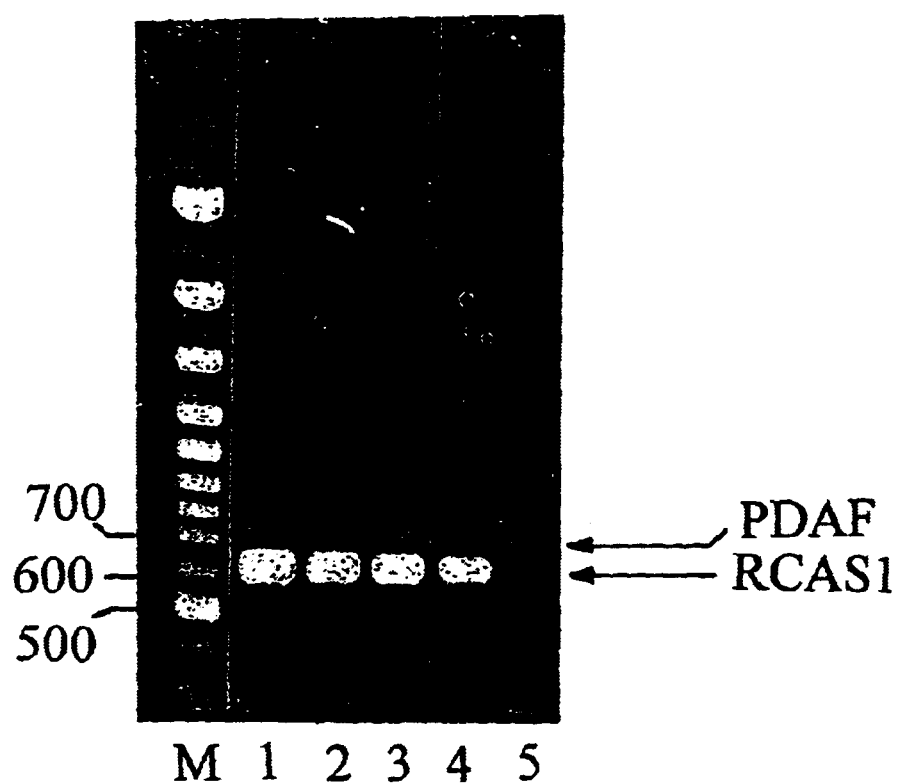
FIG. 5 shows the expression of RCAS1 and PDAF in various human tumor cell lines.

Human mammary gland adenocarcinoma MCF-7, human colorectal adenocarcinoma HT29, human melanoma A375, human embryonal rhabdomyoma RD and human placenta cell were used to determine the expression of PDAF. The RNA was extracted and then the oligo-d(T)$_{12-18}$ were used as the primer for the reverse transcription reaction. The reaction products were subsequently performed PCR reaction using the sequences in the two ends of the protein translation region of PDAF gene as primers. The resulting reaction products were analyzed through agarose gel electrophoresis. As shown in FIG. 5, the above-mentioned tumor cell lines mainly express RCAS1. Only RD cell lines express few amounts of PDAF. However, the placenta cells mainly express PDAF. On the contrary, few amounts of RCAS1 were expressed in the placenta cells.

Expression and Purification of Fusion Protein

The RCAS1 gene fragments or PDAF gene fragments contained in pCR3.1 plasmid were cut by using restriction enzyme EcoRI and isolated with 1% agarose gel. The isolated DNA fragments were purified by using Gene Clean III kit. The purified DNA was ligated to pGEX-3X vector (Amersham Pharmacia) and then the vector was transformed into E. Coli. The plasmids contained in the cells were extracted to obtain the plasrids pGEX-3X/RCAS1 and pGEX-3X/PDAF. The above two plasmids were transformed into E. Coli BL21 to express the fusion proteins.

The E. Coli cells containing the above two plasmids were cultured with shaking at 37° C. for overnight. The culture solution was inoculated to fresh AP/LB medium and cultured with shaking at 37° C. for 4 hours. 0.1 mM of IPTG was added to the culture. Then, the culture was incubated with shaking at 25° C. for 4 hours to induce the expression of the fusion proteins. The cells were centrifuged at 8000×g at 4° C. for 15 minutes to collect the cells. The cells were suspended in 20 ml of PBS buffer containing 1% Triton X-100. The cells were broken using sonicator. The insoluble precipitates were removed through centrifugation at 12,000×g at 4° C. for 15 minutes. The supernatant containing fusion protein was applied to affinity column with glutathione sepharose 4B (Amersham Pharmacia). The GST-fusion proteins were eluted with the buffer of pH8.0 containing 20 mM reduced glutathione, 120 mM NaCl, 50 mM Tris-HCl. The eluted solution was dialyzed with PBS buffer at 4° C. and concentrated with Arnicon® 8010. The concentration of the resulting proteins was determined using BCA protein assay reagent (Pierce).

The PCR was performed using primers designed from the extracellular protein regions of RCAS1 and PDAF to largely obtain the gene fragments encoding the extracellular protein regions of RCAS1 and PDAF. The gene fragments were treated with restriction enzyme BamHI and ligated to the vector pET32a(+) (Invitrogen) which was pretreated with BamHI. Then, the vector was transformed into E. Coli cells. The plasmids pET32a(+)/RCAS1.ECD and pET32a(+)/PDAF.ECD could be obtained through PCR, plasmid extraction and restriction map assay. The E. Coli BL21 (DE3) pLysS (Promega) were transformed with the above two plasmids.

Figure 6:
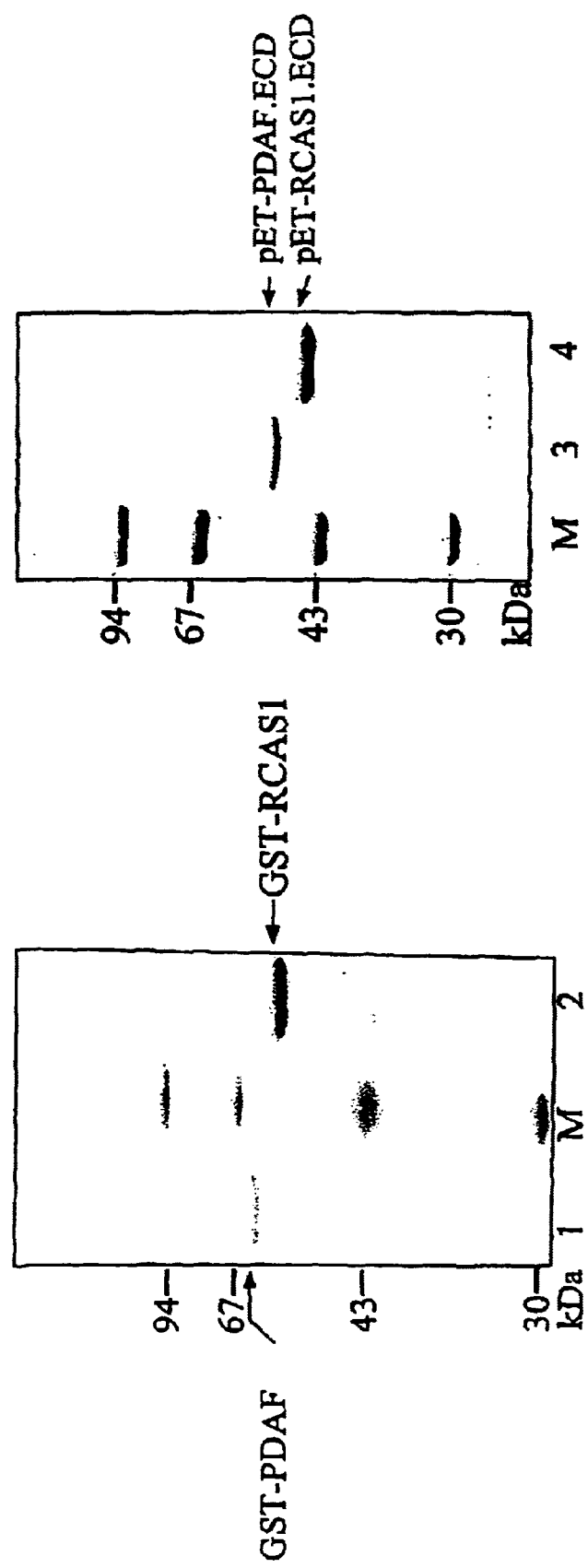
FIG. 6 shows the recombinant fusion proteins GST-RCAS1, GST-PDAF, pET-PDAF.ECD and pET-RCAS1.ECD.

The E. coli cells containing the plasmids pET32a(+)/RCAS.ECD and pET32a(+)PDAF.ECD were incubated with shaking at 37° C. for overnight. The culture was inoculated to fresh AP/LB medium and subsequently incubated with shaking at 37° C. for 3 hours. 0.1 mM of IPTG was added to the medium for inducing the large expression of the fusion protein. The culture was centrifuged at 8,000×g at 4° C. for 15 minutes to collect the cells. The cells were suspended in the buffer containing 50 mM sodium phosphate, pH8.0, and 300 mM sodium chloride and then broken by sonication. The insoluble precipitates were removed through centrifugation at 12,000×g at 4° C. for 15 minutes. The supernatant containing fusion protein was applied to an affinity column consisting of Ni-NTA SUPERFLOW (QIAGEN). The pET-fusion proteins were eluted with the buffer of pH8.0 containing 10% glycerol and 0–500 mM imidazole in continuous gradients. The profile of fusion proteins pET-RCAS1.ECD, pET-PDAF.ECD, GST-RCAS1 and GST-PDAF was shown in FIG. 6. The eluted solution was dialyzed with PBS buffer at 4° C. and concentrated with AMICON® 8010 (ultrafiltration cell). The concentration of the resulting proteins was determined using BCA protein assay reagent (Pierce).

Example 2

Figure 7:
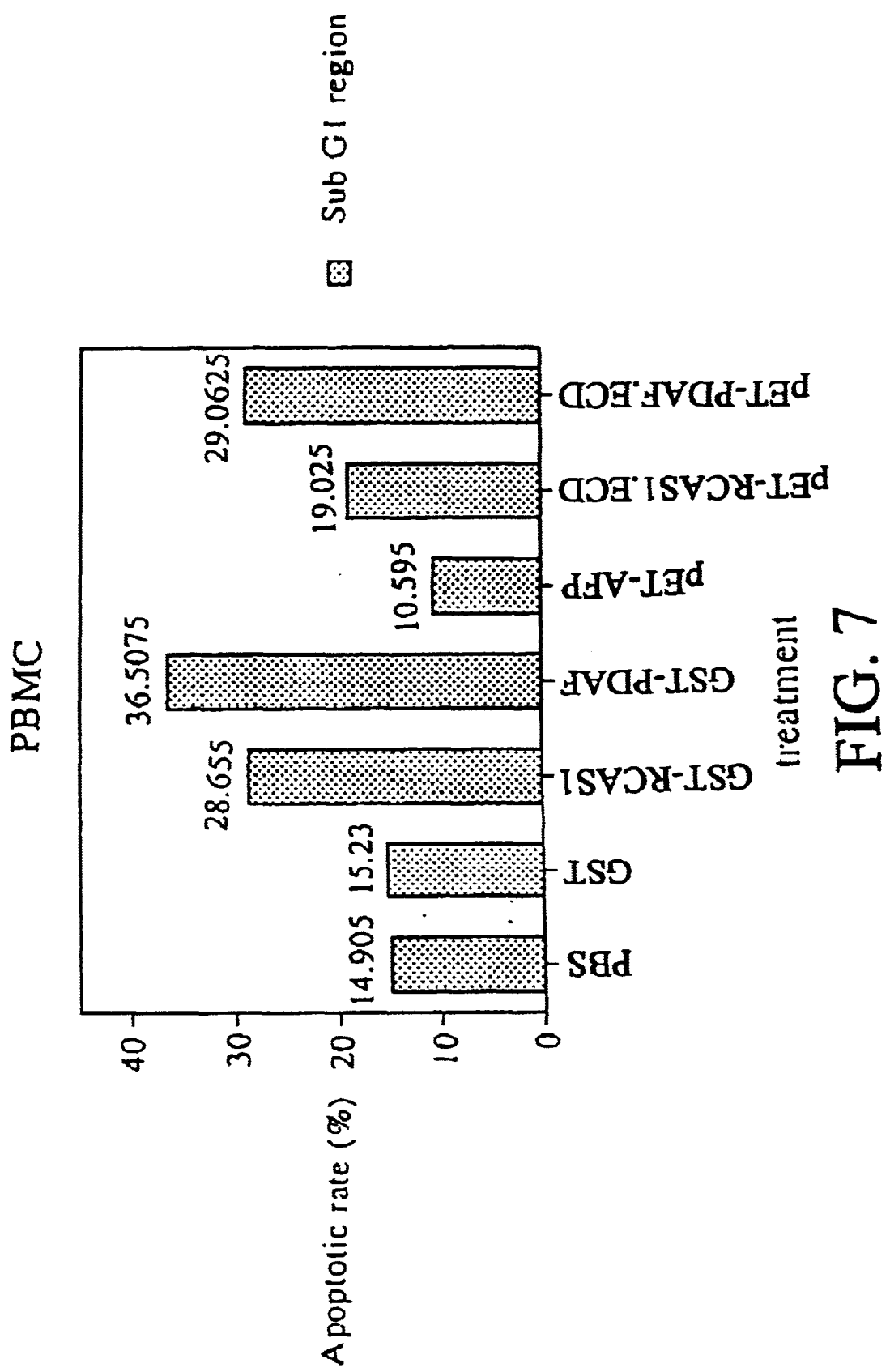
FIG. 7 shows the apoptotic rate of PBMC cell line after the treatment of RCAS1, PDAF, RCAS1.ECD, and PDAF-.ECD.

PI Staining and Flow Cytometry Assay $10^8$ of human peripheral blood mononuclear cell were incubated in RPMI medium with 10% bovine serum at 37° C. for 1–2 hours. The suspended cells were collected and then added to a 24-well culture dish coated with rabbit-anti-human immunoglobin IgM antibodies (CAPPEL). The culture dish was placed at room temperature for 1 hour for the attachment reaction. The lymphocytes attached to the rabbit-anti-human immunoglobin IgM antibodies were native B cells. The suspended cells were collected and $1×10^6$ cells/ml/well were added to a 24-well culture dish coated with mice-anti-human CD3 monoclonal antibodies (OKT3; 3 μg/ml; 1 ml/well). The lymphocytes in the dish mainly were the active T cells. The fusion proteins prepared as described above were added to the 24-well culture dishes containing the above-mentioned B and T cells, and then the dishes were placed in a incubator and incubated with 5% $CO_2$ at 37° C. for 64–68 hours. The cells were centrifuged at 2400 rpm for 5 minutes. The supernanent was removed and the hypotonic DNA staining buffer (3.5 mM sodium citrate, 0.3% Triton X-100, pH 6.8) was added to the cells. 800 μl of hypotonic DNA staining buffer and 30 μg RNase A and 5 μg propidium iodide were further added. The reaction was carried out for 30 minutes. The staining results were determined by flow cytometry. As shown in FIG. 7, the apoptotic rate of PBMC treated with GST-PDAF is higher than that of PBMC treated with GST-RCAS1.

Figure 8:
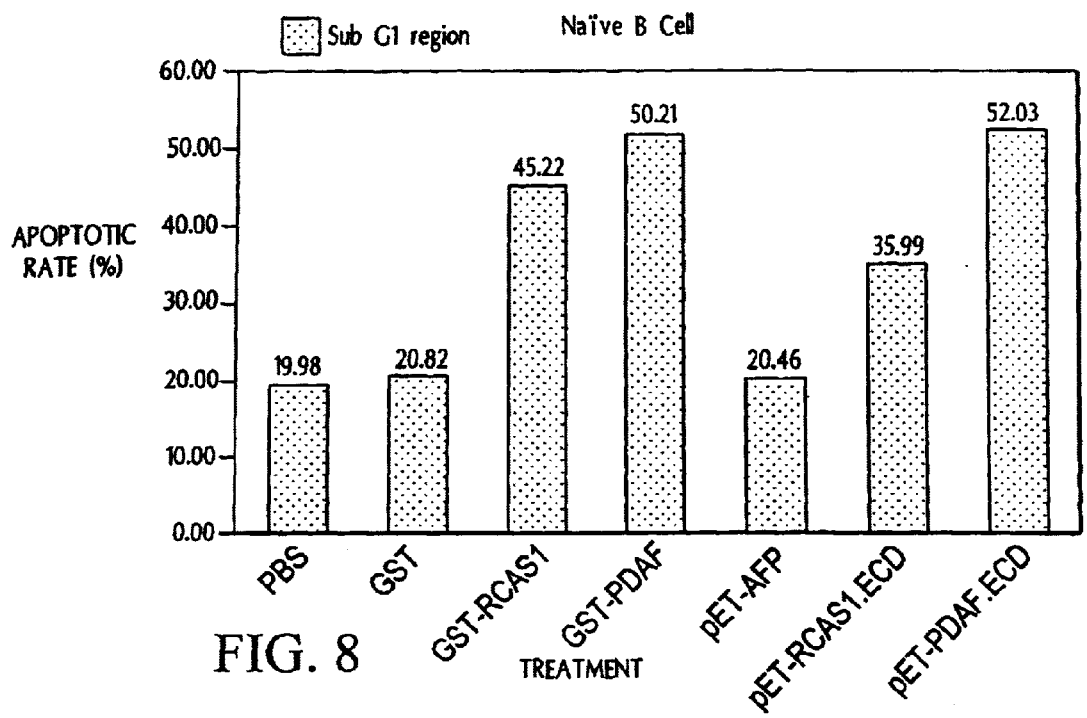
FIG. 8 shows the apoptotic rate of nAÏve B cell line after the treatment of RCAS1, PDAF, RCAS1.ECD, and PDAF-.ECD.
Figure 9:
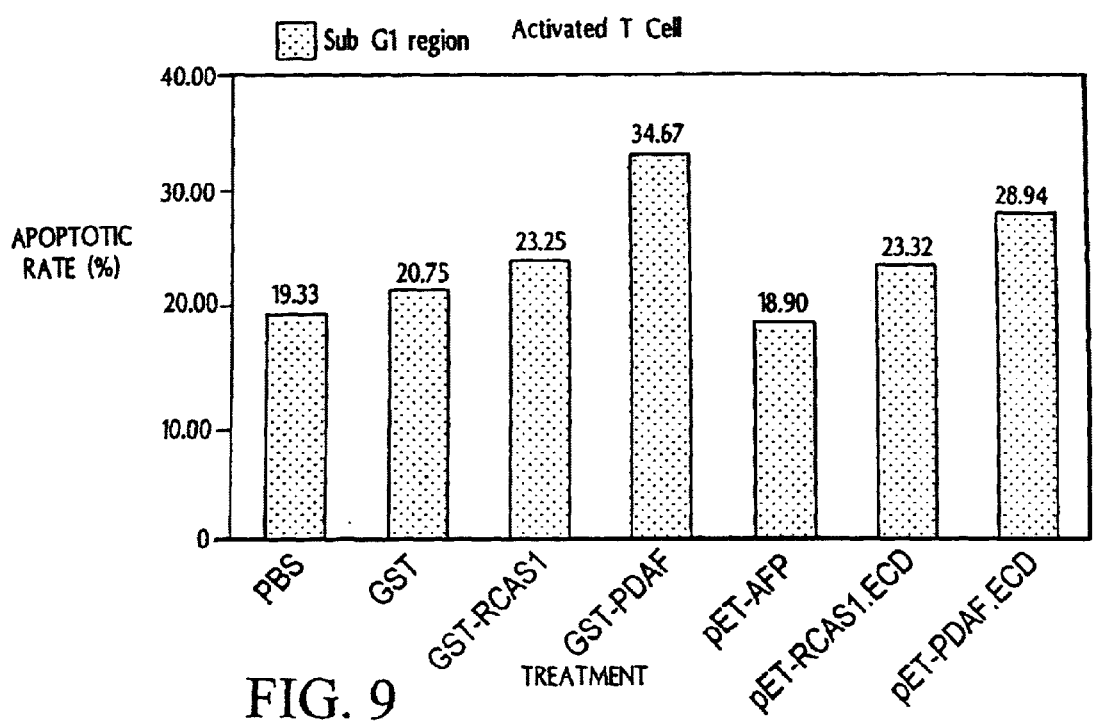
FIG. 9 shows the apoptotic rate of T cell line after the treatment of RCAS1, PDAF, RCAS1.ECD, and PDAF.ECD.

FIGS. 8 and 9 show that the GST-PDAF can induce higher apoptosis in naïve B cell and activated T cell than GST-RCAS1.

Figure 10:
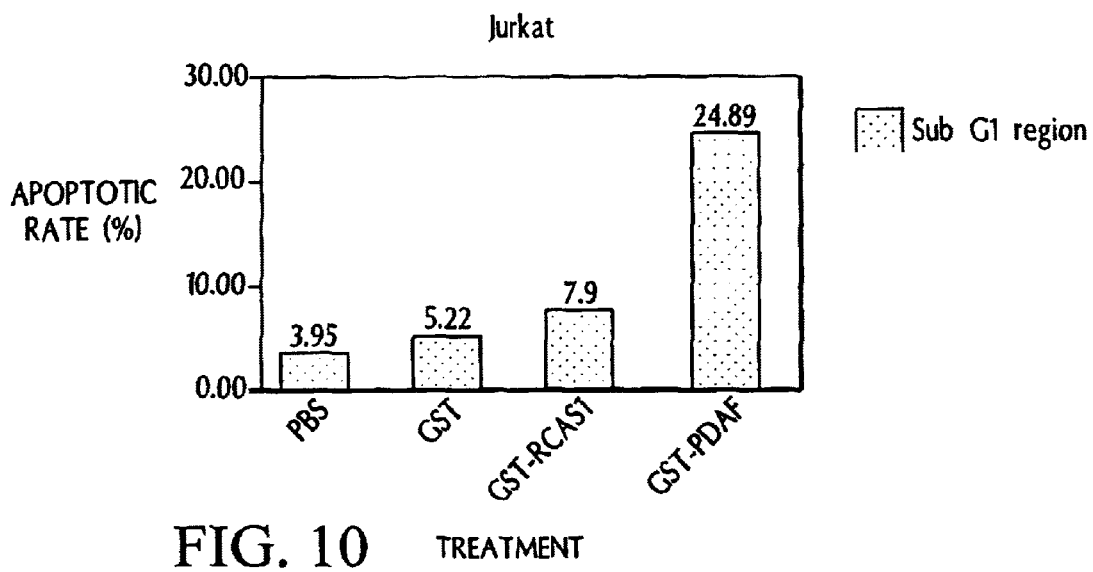
FIG. 10 shows the apoptotic rate of Jurkat cell line after the treatment of the RCAS1 and PDAF.

The PI staining and flow cytometry for human leukemia cell lines, Jurkat (T lymphoblast) and human erythroleukernia cell line, TF-1 (ATCC CRL-2003) were carried as described above. As shown in FIG. 10, the apoptotic rates of Jurkat cell treated with PBS buffer or GST protein (Control) were 3.95% and 5.22% respectively. The apoptotic rate of Jurkat cell treated with GST-RCAS1 was 7.9%, slightly higher than that of Jurkat cell treated with GST protein. However, the apoptotic rate of Jurket cell treated with GST-PDAF was largely higher than that of Jurkat cell treated with GST-RCAS1 and GST. Given the above, the PDAF of the invention can induce higher apoptosis in Jurkat cell than RCAS1.

Figure 11:
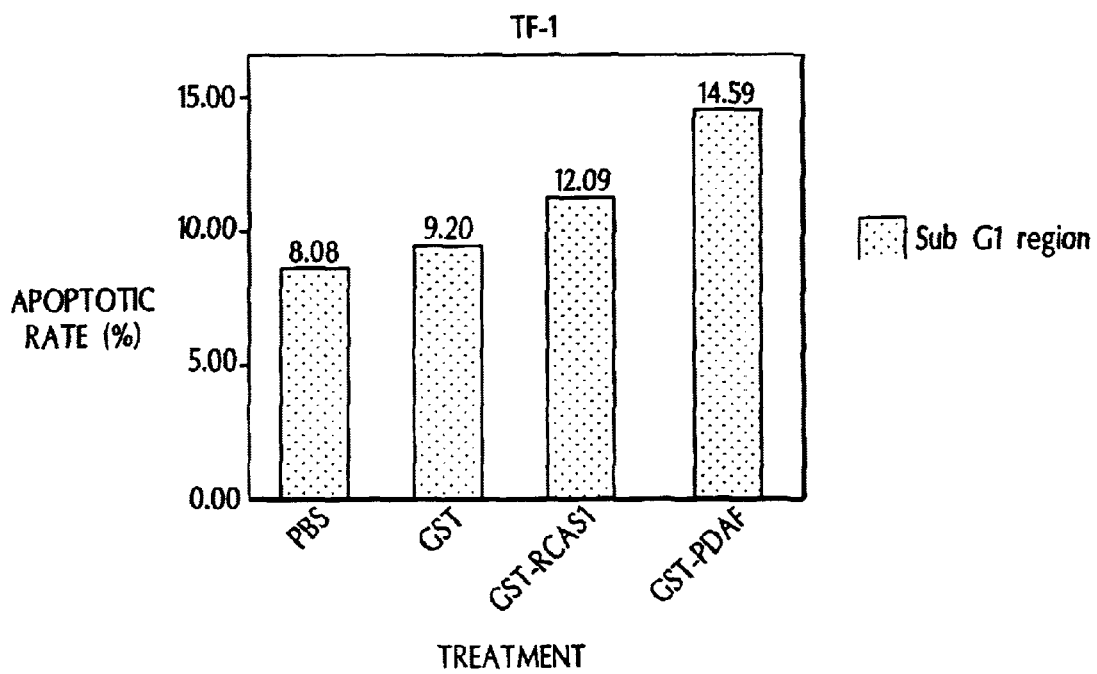
FIG. 11 shows the apoptotic rate of TF-1 cell line after the treatment of RCAS1 and PDAF.

Erythroleukemia cell line TF-1 is a hemopoietic cell line with low differentiation. As shown in FIG. 11, the PDAF of the invention can induce higher apoptosis in TF-1 cell than RCAS1.

SEQUENCE LISTING

<160> NUMBER OF SEQ ID NOS: 6

<210> SEQ ID NO 1
<211> LENGTH: 258
<212> TYPE: PRT

```
<213> ORGANISM: PDAF Polypeptide Sequence

<400> SEQUENCE: 1

Met Ala Ile Thr Gln Phe Arg Leu Phe Lys Phe Cys Thr Cys Leu Ala
 1               5                  10                  15

Thr Val Phe Ser Phe Leu Lys Arg Leu Ile Cys Arg Ser Gly Arg Gly
                20                  25                  30

Arg Lys Leu Ser Gly Asp Gln Ile Thr Leu Pro Thr Thr Val Asp Tyr
            35                  40                  45

Ser Ser Val Pro Lys Gln Thr Asp Val Glu Glu Trp Thr Ser Trp Asp
     50                  55                  60

Glu Asp Ala Pro Thr Ser Val Lys Ile Glu Gly Gly Asn Gly Asn Val
 65                  70                  75                  80

Ala Thr Gln Gln Asn Ser Leu Glu Gln Leu Glu Pro Asp Tyr Phe Lys
                 85                  90                  95

Asp Met Thr Pro Thr Ile Arg Lys Thr Gln Lys Ile Val Ile Lys Lys
            100                 105                 110

Arg Glu Pro Leu Asn Phe Gly Ile Pro Asp Gly Ser Thr Gly Phe Ser
        115                 120                 125

Ser Arg Leu Ala Ala Thr Gln Asp Leu Pro Phe Ile His Gln Ser Ser
130                 135                 140

Glu Leu Gly Asp Leu Asp Thr Trp Gln Glu Asn Thr Asn Ala Trp Glu
145                 150                 155                 160

Glu Glu Glu Asp Ala Ala Trp Gln Ala Glu Val Leu Arg Ser Arg
                165                 170                 175

Thr Asn Val Cys Leu Leu Cys Ser Leu Leu Phe His His Pro Thr Pro
                180                 185                 190

Thr Ser Thr Pro Tyr Ile Asn Gln Ser Val Lys Ile Glu Arg Val Ser
            195                 200                 205

Leu Gly Gln Trp Ser Tyr Gly Lys Ser Lys Glu Gln Gln Lys Leu Ala
        210                 215                 220

Asp Arg Glu Lys Arg Ala Ala Glu Gln Gln Arg Lys Lys Met Glu Lys
225                 230                 235                 240

Glu Ala Gln Arg Leu Met Lys Lys Glu Gln Asn Lys Ile Gly Val Lys
                245                 250                 255

Leu Ser

<210> SEQ ID NO 2
<211> LENGTH: 45
<212> TYPE: PRT
<213> ORGANISM: Amino Acids in PDAF

<400> SEQUENCE: 2

Ser Arg Thr Asn Val Cys Leu Leu Cys Ser Leu Leu Phe His His Pro
 1               5                  10                  15

Thr Pro Thr Ser Thr Pro Tyr Ile Asn Gln Ser Val Lys Ile Glu Arg
                20                  25                  30

Val Ser Leu Gly Gln Trp Ser Tyr Gly Lys Ser Lys Glu
            35                  40                  45

<210> SEQ ID NO 3
<211> LENGTH: 84
<212> TYPE: PRT
<213> ORGANISM: Amino Acids in PDAF

<400> SEQUENCE: 3
```

```
Ser Arg Thr Asn Val Cys Leu Leu Cys Ser Leu Leu Phe His His Pro
 1               5                  10                  15

Thr Pro Thr Ser Thr Pro Tyr Ile Asn Gln Ser Val Lys Ile Glu Arg
                 20                  25                  30

Val Ser Leu Gly Gln Trp Ser Tyr Gly Lys Ser Lys Glu Gln Gln Lys
             35                  40                  45

Leu Ala Asp Arg Glu Lys Arg Ala Ala Glu Gln Arg Lys Lys Met
         50                  55                  60

Glu Lys Glu Ala Gln Arg Leu Met Lys Lys Glu Gln Asn Lys Ile Gly
 65                  70                  75                  80

Val Lys Leu Ser
```

<210> SEQ ID NO 4
<211> LENGTH: 774
<212> TYPE: DNA
<213> ORGANISM: PDAF DNA Sequence

<400> SEQUENCE: 4

```
atggccatca cccagtttcg gttatttaaa ttttgtacct gcctagcaac agtattctca    60
ttcctaaaga gattaatatg cagatctggc agaggacgga aattaagtgg agaccaaata   120
actttgccaa ctacagttga ttattcatca gttcctaagc agacagatgt tgaagagtgg   180
acttcctggg atgaagatgc acccaccagt gtaaagatcg aaggagggaa tgggaatgtg   240
gcaacacaac aaaattcttt ggaacaactg gaacctgact attttaagga catgacacca   300
actattagga aaactcagaa aattgttatt aagaagagag aaccattgaa ttttggcatc   360
ccagatggga gcacaggttt ctctagtaga ttagcagcta caagatctg cctttttatt   420
catcagtctt ctgaattagg tgacttagat acctggcagg aaaataccaa tgcatgggaa   480
gaagaagaag atgcagcctg caagcagaa gaagttctga tccaggac caatgtatgt   540
ttactctgct ctctcctgtt tcatcatccc actcctacct ccactcccta cattaaccaa   600
tcagtaaaga tagagagagt gagtctgggt cagtggagtt acggaaagag taaggaacag   660
cagaaactag cagacagaga aagagagca gccgaacaac aaaggaagaa atggaaaag   720
gaagcacaac ggctaatgaa gaaggaacaa acaaaattg tgtgaaact ttca           774
```

<210> SEQ ID NO 5
<211> LENGTH: 135
<212> TYPE: DNA
<213> ORGANISM: Nucleotides in PDAF DNA Sequence

<400> SEQUENCE: 5

```
tccaggacca atgtatgttt actctgctct ctcctgtttc atcatcccac tcctacctcc    60
actccctaca ttaaccaatc agtaaagata gagagagtga gtctgggtca gtggagttac   120
ggaaagagta aggaa                                                    135
```

<210> SEQ ID NO 6
<211> LENGTH: 252
<212> TYPE: DNA
<213> ORGANISM: Nucleotides in PDAF DNA Sequence

<400> SEQUENCE: 6

```
tccaggacca atgtatgttt actctgctct ctcctgtttc atcatcccac tcctacctcc    60
actccctaca ttaaccaatc agtaaagata gagagagtga gtctgggtca gtggagttac   120
ggaaagagta aggaacagca gaaactagca gacagagaaa agagagcagc cgaacaacaa   180
```

```
aggaagaaaa tggaaaagga agcacaacgg ctaatgaaga aggaacaaaa caaaattggt    240 gtgaaactتt ca                                                        252
```

What is claimed is:

1. A polypeptide, which comprises the amino acid sequence of SEQ ID NO:1.

2. The polypeptide as claimed in claim 1, which induces apoptosis.

3. A composition comprising the polypeptide as claimed in claim 1 and a pharmaceutically acceptable carrier.

4. The polypeptide of claim 1, wherein the polypeptide consists of the amino acid sequence of SEQ ID NO:1.

5. A polypeptide, which consists of the extracellular domain (amino acids 29–258) of SEQ ID NO:1.

6. A composition comprising the polypeptide of claim 4 and a pharmaceutically acceptable carrier.

7. A composition comprising the polypeptide of claim 5 and a pharmaceutically acceptable carrier.

8. A polypeptide, which consists of the amino acid sequence of SEQ ID NO:2.

9. A polypeptide, which consists of the amino acid sequence of SEQ ID NO:3.

10. A composition comprising the polypeptide of claim 8 and a pharmaceutically acceptable carrier.

11. A composition comprising the polypeptide of claim 9 and a pharmaceutically acceptable carrier.

* * * * *

UNITED STATES PATENT AND TRADEMARK OFFICE
CERTIFICATE OF CORRECTION

PATENT NO.   : 6,689,867 B1
DATED        : February 10, 2004
INVENTOR(S)  : Wei-Yu Lo and Shie-Liang Hsieh It is certified that error appears in the above-identified patent and that said Letters Patent is hereby corrected as shown below:

Column 2,
Line 48, replace "nAÏve" with -- naïve --.

Column 3,
Line 54, delete "/" between "and" and "expression".

Column 4,
Line 46, replace "tumor" with -- tumors --.
Line 54, replace "IN" with -- ID --.

Column 5,
Line 31, insert -- . -- after "art".

Column 6,
Line 43, replace "unimunosuppressive" with -- immunosuppressive --.
Line 51, replace "Pharmacezitical" with -- Pharmaceutical --.

Column 7,
Line 19, replace "intoruced" with -- introduced --.

Column 8,
Line 18, replace "traslation" with -- translation --.
Line 20, insert -- ) -- between "4" and ".".
Line 35, replace "phosphatidylinositol" with -- phosphatidyllinositol --.
Line 40, replace "DNAISIS" with -- DNA1SIS --.

Column 9,
Line 3, replace "plasrids" with -- plasmids --.
Line 23, replace "Arnicon®" with -- Amicon® --.

UNITED STATES PATENT AND TRADEMARK OFFICE
CERTIFICATE OF CORRECTION

PATENT NO. : 6,689,867 B1
DATED : February 10, 2004
INVENTOR(S) : Wei-Yu Lo and Shie-Liang Hsieh It is certified that error appears in the above-identified patent and that said Letters Patent is hereby corrected as shown below:

<u>Column 10,</u>
Line 25, before "incubator" replace "a" with -- an --.

Signed and Sealed this

Fifteenth Day of June, 2004

JON W. DUDAS
*Acting Director of the United States Patent and Trademark Office*